US010412377B2

(12) United States Patent
Forthmann et al.

(10) Patent No.: US 10,412,377 B2
(45) Date of Patent: Sep. 10, 2019

(54) AUGMENTED DISPLAY DEVICE FOR USE IN A MEDICAL IMAGING LABORATORY

(71) Applicant: KONINKLIJKE PHILIPS N.V., Eindhoven (NL)

(72) Inventors: Peter Forthmann, Latham, NY (US); Glen Pfleiderer, Katonah, NY (US)

(73) Assignee: Koninklijke Philips N.V., Eindhoven (NL)

( * ) Notice: Subject to any disclaimer, the term of this patent is extended or adjusted under 35 U.S.C. 154(b) by 192 days.

(21) Appl. No.: 15/403,432

(22) Filed: Jan. 11, 2017

(65) Prior Publication Data

US 2018/0197337 A1 Jul. 12, 2018

(51) Int. Cl.
| | |
|---|---|
| *H04N 13/344* | (2018.01) |
| *G06F 3/01* | (2006.01) |
| *H04N 13/239* | (2018.01) |
| *H04N 13/383* | (2018.01) |
| *A61B 6/00* | (2006.01) |
| *G06F 3/0481* | (2013.01) |

(Continued)

(52) U.S. Cl.
CPC ........... *H04N 13/344* (2018.05); *A61B 6/466* (2013.01); *G06F 3/012* (2013.01); *G06F 3/013* (2013.01); *G06F 3/04815* (2013.01); *G06T 3/00* (2013.01); *G06T 11/60* (2013.01); *H04N 13/239* (2018.05); *H04N 13/383* (2018.05); *A61B 6/032* (2013.01); *A61B 6/037* (2013.01); *H04N 5/2224* (2013.01); *H04N 5/23238* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,672,649 A | * | 6/1987 | Rutt | A61B 6/032 378/10 |
| 6,774,929 B1 | | 8/2004 | Kopp | |

(Continued)

FOREIGN PATENT DOCUMENTS

CN 203774039 U 8/2014

OTHER PUBLICATIONS

Garcia-Palacios et al "Use of Virtual Reality Distraction to Reduce Claustrophobia Symptoms . . . " Cyber Psychology and Behavior, vol. 10, No. 3, 2007, pp. 485-489.

*Primary Examiner* — Hilina K Demeter

(57) ABSTRACT

An augmented reality device used in a medical imaging laboratory housing a medical imaging device (10) includes a headset (30), cameras (32, 33) mounted in the medical imaging laboratory, and directional sensors (34, 35, 36, 37) mounted on the headset. The cameras generate a panorama image (54). Data collected by the directional sensors is processed to determine the viewing direction (60). The panorama image and the determined viewing direction are processed to generate an augmented patient view image (80) in which the medical imaging device is removed, replaced, or made partially transparent, the augmented image is presented on a display (40) of the headset. The directional sensors may include a headset camera (34) that provides a patient view image (50), which is augmented by removing or making partially transparent any portion of the medical imaging device in the patient view image by substituting corresponding portions of the panorama image.

21 Claims, 4 Drawing Sheets

(51) Int. Cl.
*G06T 3/00* (2006.01)
*G06T 11/60* (2006.01)
*H04N 5/232* (2006.01)
*A61B 6/03* (2006.01)
*H04N 5/222* (2006.01)

(56) References Cited

U.S. PATENT DOCUMENTS

| | | | | |
|---|---|---|---|---|
| 9,101,279 | B2* | 8/2015 | Ritchey | G16H 40/63 |
| 9,547,940 | B1* | 1/2017 | Sun | G06T 19/006 |
| 9,675,319 | B1* | 6/2017 | Razzaque | A61B 8/0841 |
| 9,892,564 | B1* | 2/2018 | Cvetko | G06T 19/006 |
| 10,013,808 | B2* | 7/2018 | Jones | G06F 3/012 |
| 2003/0128034 | A1 | 7/2003 | Haumann | |
| 2009/0268867 | A1* | 10/2009 | Mori | A61B 6/14 |
| | | | | 378/39 |
| 2010/0302347 | A1* | 12/2010 | Shikata | H04N 5/232 |
| | | | | 348/36 |
| 2014/0275760 | A1* | 9/2014 | Lee | A61B 1/00045 |
| | | | | 600/102 |
| 2015/0222880 | A1* | 8/2015 | Choi | G03B 37/04 |
| | | | | 348/43 |
| 2015/0281680 | A1* | 10/2015 | Grafenberg | A61B 6/4441 |
| | | | | 348/50 |
| 2015/0306340 | A1 | 10/2015 | Giap et al. | |
| 2015/0309316 | A1* | 10/2015 | Osterhout | G06F 3/012 |
| | | | | 345/8 |
| 2016/0058387 | A1 | 3/2016 | Kobayashi | |
| 2016/0065856 | A1* | 3/2016 | Sohn | H04N 5/23258 |
| | | | | 348/333.11 |
| 2016/0109642 | A1 | 4/2016 | Pei et al. | |
| 2016/0142703 | A1* | 5/2016 | Park | G09G 3/001 |
| | | | | 348/39 |
| 2016/0206263 | A1* | 7/2016 | Ruppertshofen | A61B 6/10 |
| 2016/0242728 | A1* | 8/2016 | Niizeki | A61B 6/547 |
| 2016/0301866 | A1* | 10/2016 | Kim | G10L 25/87 |
| 2016/0335742 | A1* | 11/2016 | Yim | A61B 6/032 |
| 2017/0186157 | A1* | 6/2017 | Boettger | G06T 7/50 |

* cited by examiner

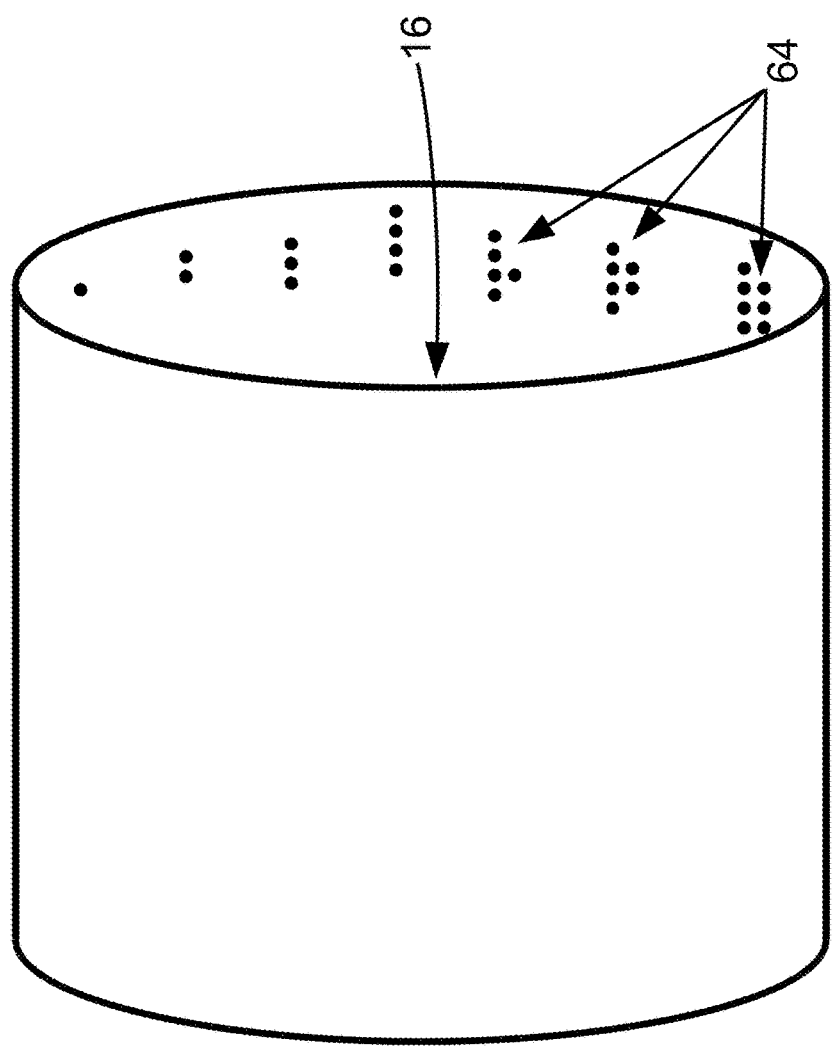

AUGMENTED DISPLAY DEVICE FOR USE IN A MEDICAL IMAGING LABORATORY

FIELD

The following relates generally to the medical imaging arts, magnetic resonance imaging (MRI) arts, medical arts, patient well-being maintenance arts, and related arts.

BACKGROUND

Many medical imaging devices employ a bore-type arrangement, in which the device has a generally cylindrical housing defining a central bore. By way of illustration, many magnetic resonance imaging (MRI) devices (i.e. "scanners") have a cylindrical housing containing a solenoidal-type magnet that generates a longitudinal or "axial" static magnetic field (usually denoted the $B_0$ field) in the bore. The cylindrical MRI housing may contain other components, such as magnetic field gradient coils and a "whole body" radio frequency coil. As another illustrative example, a positron emission tomography (PET) imaging device or scanner typically has a cylindrical housing containing one or more PET radiation detector rings. As yet another illustrative example, a transmission computed tomography (CT) imaging device has a cylindrical housing containing an x-ray tube and an x-ray detector array mounted facing the x-ray tube on a rotating annular gantry.

In such imaging devices, the imaging subject (e.g. patient) is moved via a table or other support into the central bore for imaging. The bore presents a relatively small-diameter mostly enclosed space to the patient, and being placed into the bore can trigger claustrophobia in patients who may be susceptible to this condition. Even patients who are not ordinarily prone to claustrophobia may find loading into the bore to be an anxiety-inducing experience, especially if the patient is already under stress due to medical difficulties and/or due to uncertainty as to the potential adverse medical findings that may be revealed by the imaging examination.

The use of virtual reality (VR) is a known approach for alleviating patient anxiety during MRI examinations. For example, CinemaVision™ is a VR product available from Resonance Technology Inc. (Northridge, Calif., USA). CinemaVision™ includes a VR audio/video headset which presents the patient with a soothing VR experience during the MRI procedure. VR is also used in conjunction with functional MRI (fMRI) brain imaging in order to present the patient with audio/video stimulation useful for probing brain activity. For example, Resonance Technology Inc. provides the VisuaStimDigital™ virtual reality product for use in providing fMRI stimulation.

The following discloses certain improvements.

SUMMARY

In one disclosed aspect, an augmented reality device is disclosed for use in a medical imaging laboratory housing a medical imaging device. The augmented reality device includes a headset having a display mounted on the headset to be viewed by an imaging subject when the headset is worn by the imaging subject, cameras mounted in the medical imaging laboratory, directional sensors mounted on the headset to collect data indicative of a viewing direction of the imaging subject, and at least one electronic processor. At least one non-transitory storage medium stores: panorama image generating instructions readable and executable by the at least one electronic processor to stitch together images acquired by the cameras to generate a panorama image of the medical imaging laboratory; viewing direction analysis instructions readable and executable by the at least one electronic processor to process the data indicative of the viewing direction of the imaging subject collected by the directional sensors and to output a determined viewing direction; augmentation instructions readable and executable by the at least one electronic processor to process at least the panorama image and the determined viewing direction to generate an augmented patient view image corresponding to the determined viewing direction and augmented at least by the medical imaging device being removed, replaced, or made partially transparent in the augmented patient view image; and headset operating instructions readable and executable by the at least one electronic processor to operate the headset to present the augmented patient view image using the display mounted on the headset.

In another disclosed aspect, an augmented reality method is disclosed for use in a medical imaging laboratory housing a medical imaging device. A panorama image of the medical imaging laboratory is acquired using cameras mounted in the medical imaging laboratory. A viewing direction of an imaging subject is determined using an electronic processor operating on data acquired by directional sensors mounted on a headset worn by the imaging subject. At least the panorama image and the determined viewing direction are processed using the electronic processor to generate an augmented patient view image corresponding to the determined viewing direction and augmented at least by the medical imaging device being removed, replaced, or made partially transparent in the augmented patient view image. The augmented patient view image is presented to the imaging subject using a display mounted on the headset worn by the imaging subject.

One advantage resides in providing a virtual reality device for reducing patient anxiety during an MRI examination or other imaging procedure while ensuring the patient retains awareness of the physical surroundings of the imaging laboratory.

Another advantage resides in providing a virtual reality device for reducing patient anxiety during an MRI examination or other imaging procedure while ensuring the patient retains situational awareness in order to provide effective assist or cooperation.

Another advantage resides in providing a virtual reality device for reducing patient anxiety during an MRI examination or other imaging procedure with reduced potential for patient injury.

Another advantage resides in providing a virtual reality device for reducing patient anxiety during an MRI examination or other imaging procedure while ensuring the patient retains normal hearing capacity.

Another advantage resides in providing a virtual reality device for reducing patient anxiety during an MRI examination or other imaging procedure while ensuring the patient maintains the mental capacity and situational awareness to provide informed consent.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 4 diagrammatically illustrates an embodiment of the MRI bore including positional markers to assist in view direction analysis.

DETAILED DESCRIPTION

Figure 1:
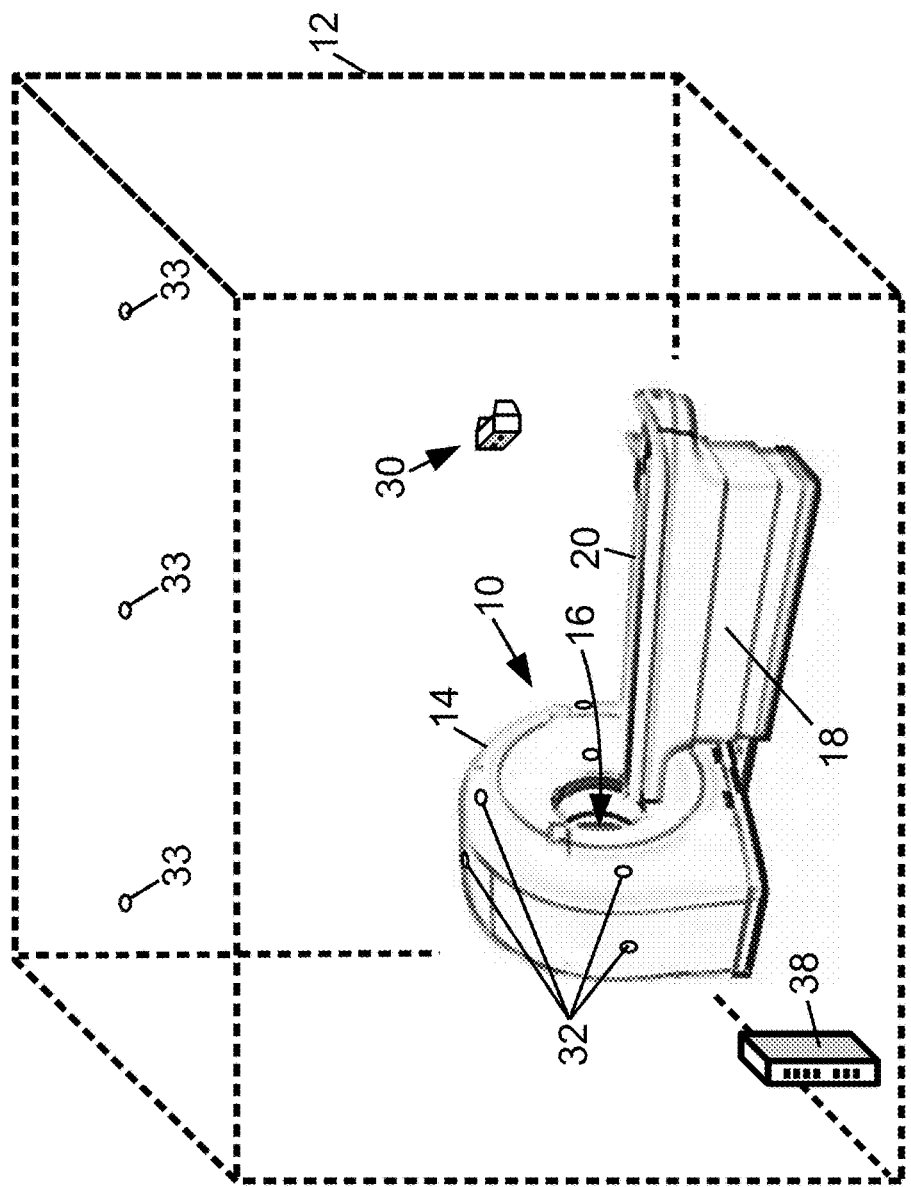
FIG. 1 diagrammatically illustrates a magnetic resonance imaging (MRI) laboratory including an augmented reality device for reducing patient anxiety.

With reference to FIG. 1, an illustrative magnetic resonance imaging (MRI) laboratory includes an MRI imaging device 10, commonly referred to as an MRI scanner 10, disposed in a radio frequency (RF) shielded room 12 comprising an enclosing Faraday cage to shield the MRI scanner 10 from outside radio frequency interference (RFI) and to reduce or eliminate RFI produced by the MRI scanner 10 from interfering with outside electronic equipment or devices. The MRI scanner 10 includes a housing 14 with (i.e. defining) a bore 16 into which an imaging subject is received for imaging. A couch 18 or other subject support is provided, with a tabletop 20 on which the patient or other imaging subject is placed. The tabletop 20 is movable into the bore 16 either manually or via a motorized mechanism. The illustrative housing 14 is generally cylindrical housing and contains a solenoidal-type magnet that generates a longitudinal or "axial" static magnetic field (usually denoted the $B_0$ field) in the bore 16, magnetic field gradient coils for superimposing magnetic field gradients, an optional "whole body" radio frequency coil, and optionally other components (components internal to the housing 14 not shown).

While the illustrative example is an MRI, the disclosed patient soothing augmented reality devices may be employed in conjunction with other types of medical imaging devices, such as a positron emission tomography (PET) imaging device or scanner which typically has a cylindrical housing containing one or more PET radiation detector rings; or a transmission computed tomography (CT) imaging device which typically has a cylindrical housing containing an x-ray tube and an x-ray detector array mounted facing the x-ray tube on a rotating annular gantry; "hybrid" medical imaging devices such as PET/CT scanners; medical imaging devices associated with other medical instrumentation, e.g. MRI-Linac systems (where "linac" denotes a linear accelerator used for delivery of radiation therapy) or interventional medical imaging devices used in conjunction with invasive medical procedures; or so forth. Each such medical imaging device includes a housing including (i.e. defining) bore into which an imaging subject (e.g. patient) is moved via a table for imaging. The bore can be a claustrophobic or otherwise anxiety-inducing environment for the patient, especially if the patient is already under stress due to medical difficulties and/or due to uncertainty as to the potential adverse medical findings that may be revealed by the imaging examination.

As previously noted, a known device for soothing the patient loaded into the bore is a virtual reality (VR) device which presents the patient with a synthetic experience that is different from, and preferably more relaxing/soothing/reassuring than, the actual medical imaging laboratory. However, it is recognized herein that for many patients such a VR synthesized experience may be unsatisfactory. The VR experience is divorced from the reality of the medical imaging laboratory, thus making the patient blind to the real environment. This loss of awareness may itself be anxiety-inducing. The loss of situational awareness may also compromise the patient's ability to participate in the medical imaging examination, for example by performing operations such as breath holds, or may lead to the patient interacting with the VR environment in undesirable ways, such as by volitional movements that interfere with the imaging. The lack of situational awareness could also adversely impact the patient's ability to provide informed consent during the examination. The VR environment also blinds the patient to the reality of the walls of the bore which closely surrounds the patient, which can lead to inadvertent collisions between moving arms or legs of the patient and the surrounding walls of the bore—such inadvertent collisions could startle or even injure the patient.

These difficulties are increased if the VR experience is maximized by providing the patient with noise-reducing earphones (e.g. noise-canceling headphones or the like) configured to reduce or block external sound. This maximizes the VR experience by ensuring the synthesized VR experience is not shattered by inconsistent sounds generated in the laboratory. However, such noise-reducing earphones further reduce the patient's situational awareness, and can prevent the patient from hearing and responding to instructions provided by medical personnel.

In embodiments disclosed herein, an augmented reality (AR) device is employed to sooth the patient. The AR device creates an augmented reality which is based on the actual medical imaging laboratory environment but is augmented at least by the medical imaging device 10 being removed, replaced, or made partially transparent in the augmented patient view image. This removes, or at least reduces the psychological impact of, the most intimidating component of the laboratory, namely the medical imaging device 10 and its claustrophobic bore 16. At the same time, as an augmented reality the AR device ensures the patient maintains situational awareness so as to avoid the uncomfortable feeling of being divorced from reality, and to facilitate rapid patient response to instructions from medical personnel. In embodiments in which the medical imaging device 10 is replaced by some other component and/or is rendered partially transparent, the patient retains awareness of the closely proximate walls of the bore 16, but the augmentation makes them less intimidating.

Figure 2:
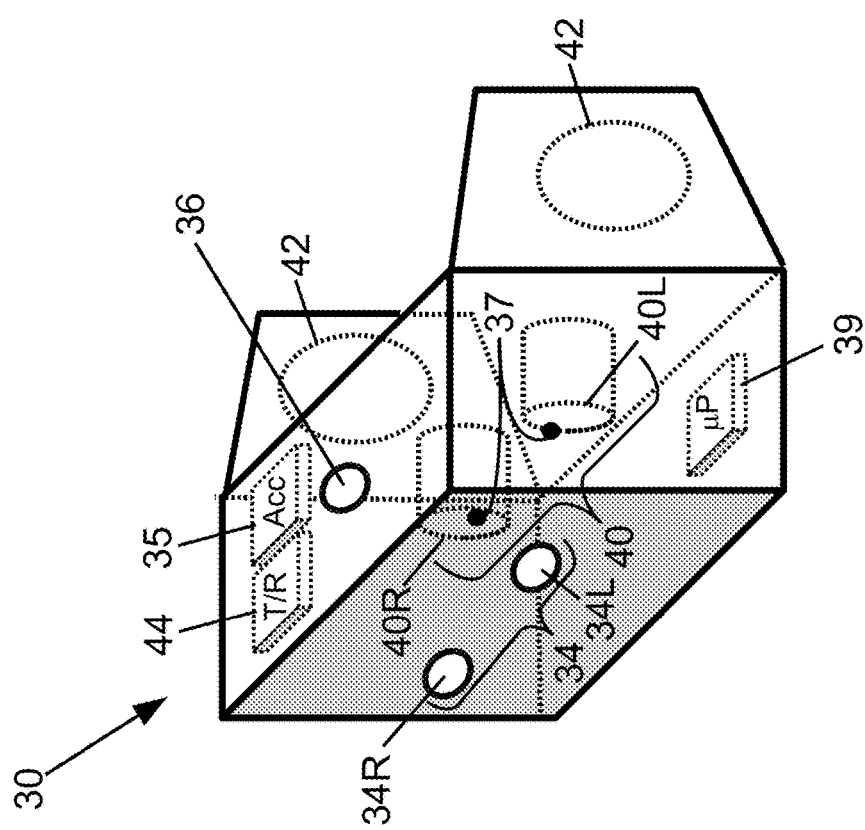
FIG. 2 shows a diagrammatic perspective view of the headset of the augmented reality device of FIG. 1.

With continuing reference to FIG. 1 and with further reference to FIG. 2, the AR device includes a headset 30, cameras 32, 33 mounted at various fixed positions in the medical imaging laboratory so as to provide a panoramic view, directional sensors 34, 35, 36, 37 mounted on the headset 30 to collect data indicative of a viewing direction of the imaging subject (see FIG. 2 showing an enlarged view of the headset 30 with selected internal components indicated), and at least one electronic processor 38, 39 e.g. embodied as an illustrative computer 38 and/or a microprocessor 39 installed in the headset 30. The microprocessor 38, 39 is connected to read and execute instructions stored on a non-transitory storage medium (not shown) to perform operations implementing the AR environment. These illustrative components are described in further detail below.

The headset 30 includes a display 40 mounted on the headset 30 to be viewed by an imaging subject when the headset is worn by the imaging subject. The illustrative display 40 is a binocular display including a left eye display 40L mounted on the headset 30 to be viewed by a left eye of the imaging subject when the headset 30 is worn by the imaging subject, and a right eye display 40R mounted on the headset 30 to be viewed by a right eye of the imaging subject when the headset is worn by the imaging subject. Alternatively, a single display may be provided which is of sufficient width to be simultaneously viewed by both left and right eyes. In general, it is contemplated for the display 40 to be either a stereoscopic display in which left and right offset images are separately presented to the left and right eye of the viewer via the respective displays 40L, 40R, or a conventional display without stereoscopic depth simulation. It should be noted that other known approaches for stereo display are contemplated, such as using a single display that time-multiplexes the left eye image and right eye image in synchronization with rapid shutter cycling of left eye and right eye shutters, for example, or using a single display showing the left eye and right eye images with different polarizations in conjunction with appropriate (different) left eye and right eye polarizer filters, as another example.

Similarly, the illustrative directional sensors 34, 35, 36, 37 mounted on the headset 30 include a stereoscopic headset camera 34 comprising a left headset camera 34L and a right headset camera 34R that operate to acquire left and right offset images, respectively, so as to provide a stereoscopic patient view image. In an alternative embodiment (not shown), the headset camera includes a single camera providing a patient view image that is conventional and does not include stereoscopic depth simulation. The illustrative directional sensors 34, 35, 36, 37 further include an accelerometer 35 to detect and quantify motion of the head to assist in analyzing the viewing direction, a top-mounted headset camera 36 to image the view above the patient's head, and eye trackers 37. The top-mounted headset camera 36 can be useful determining view direction when the patient's head (and hence the worn headset 30) is inside the bore 16 so that the patient view image shows only the (typically featureless) bore walls. The eye trackers 37 are mounted on the headset proximate to the displays 40L, 40R to view the left and/or right eye to determine ocular viewing direction. Additional or different directional sensors are also contemplated—for example, in environments that can tolerate an applied electromagnetic field (e.g. CT imaging), the directional sensors may include electromagnetic (EM) tracking sensors mounted on the headset and detected by an EM tracking system to monitor the location and orientation of the headset so as to assess view direction.

The illustrative fixed cameras 32, 33 mounted at various fixed positions in the medical imaging laboratory include illustrative MRI device-mounted cameras 32 mounted on the medical imaging device 10 and oriented to generate images looking outward from the medical imaging device 10, and ceiling-mounted cameras 33 mounted on the ceiling to provide images at further vantage points. Although not shown, wall-mounted cameras and/or otherwise-placed cameras may be distributed through the laboratory to provide a panoramic view of the laboratory. As the augmented reality view is intended to exclude the medical imaging device 10, the panoramic view may optionally not capture the MRI device 10, e.g. the cameras 32 generate images looking outward from the medical imaging device 10.

The electronic processor 38, 39 may comprise one or more microprocessor- or microcontroller-equipped electronic device(s) suitably programmed by instructions read from a non-transitory storage medium. The electronic processor 38, 39 may include a desktop computer 38, notebook computer, dedicated electronic AR controller device 39, or so forth. The illustrative electronic processors 38, 39 are located inside the MRI laboratory; in this case they should be shielded, e.g. enclosed in a metal shielding box, to avoid generating or receiving RFI. In other embodiments, the electronic processor may be located outside of the MRI laboratory and accessed via suitably shielded coaxial or triaxial cables, fiber optic cables, or the like. The non-transitory storage medium storing the instructions read and executed by the electronic processor 38, 39 may, for example, include a hard disk drive or other magnetic storage medium, an optical disk or other optical storage medium, a solid state drive (SSD), FLASH memory, or other electronic storage medium, various combinations thereof, or so forth. Such non-transitory storage medium stores instructions readable and executable by the electronic processor 38, 39 to perform the disclosed AR implementation operations.

The headset 30 may take any suitable form factor. The illustrative headset 30 comprises goggles; in another contemplated embodiment the headset may be in the form of eyeglasses. Because the AR device provides an augmented reality presentation of the laboratory augmented at least by removal, replacement, or partial transparency of the medical imaging device 10, it is contemplated to omit any sort of earphones. This is in contrast to virtual reality (VR) where suppression of sounds from the laboratory is highly advantageous to maintaining the VR illusion. By contrast, the AR device is presenting the medical imaging laboratory with augmentation, so that sounds of the laboratory are expected and do not adversely impact the augmented reality. However, in some embodiments, including the illustrative embodiment, the headset 30 is provided with earphones 42 which may optionally be noise-reducing earphones. The earphones 42 may be useful to communicate instructions from medical personnel to the patient in the imaging laboratory (which can be noisy), such as instructions to initiate or release a breath-hold. The earphones 42 may optionally be noise-reducing, which may be beneficial for the patient if the laboratory is particularly noisy—for example, operation of the magnetic field gradient coils of the illustrative MRI device 10 can produce substantial noise that can be disturbing to the patient.

The illustrative headset 30 further includes a wireless transceiver 44 for porting data to or from the headset 30. Likewise, although not illustrated the fixed cameras 32, 33 and the computer 38 suitably includes wired or wireless communication links. Depending upon the local RFI conditions and the types of signals conveyed, the communication links may include wireless transceivers, shielded coaxial or triaxial cabling, fiber optic cabling, and/or the like. In the illustrative MRI laboratory, the communication must be compatible with the high magnetic and electric fields generated by the MRI device 10, and the typically high sensitivity of the MRI imaging to RFI that may be generated by the various AR device components. By contrast, in embodiments for use in conjunction with other types of medical imaging devices such as PET or CT scanners, the RFI control may be relaxed due to the lower magnetic and electric fields generated by these imagers and/or reduced sensitivity of the imager to RFI.

Figure 3:
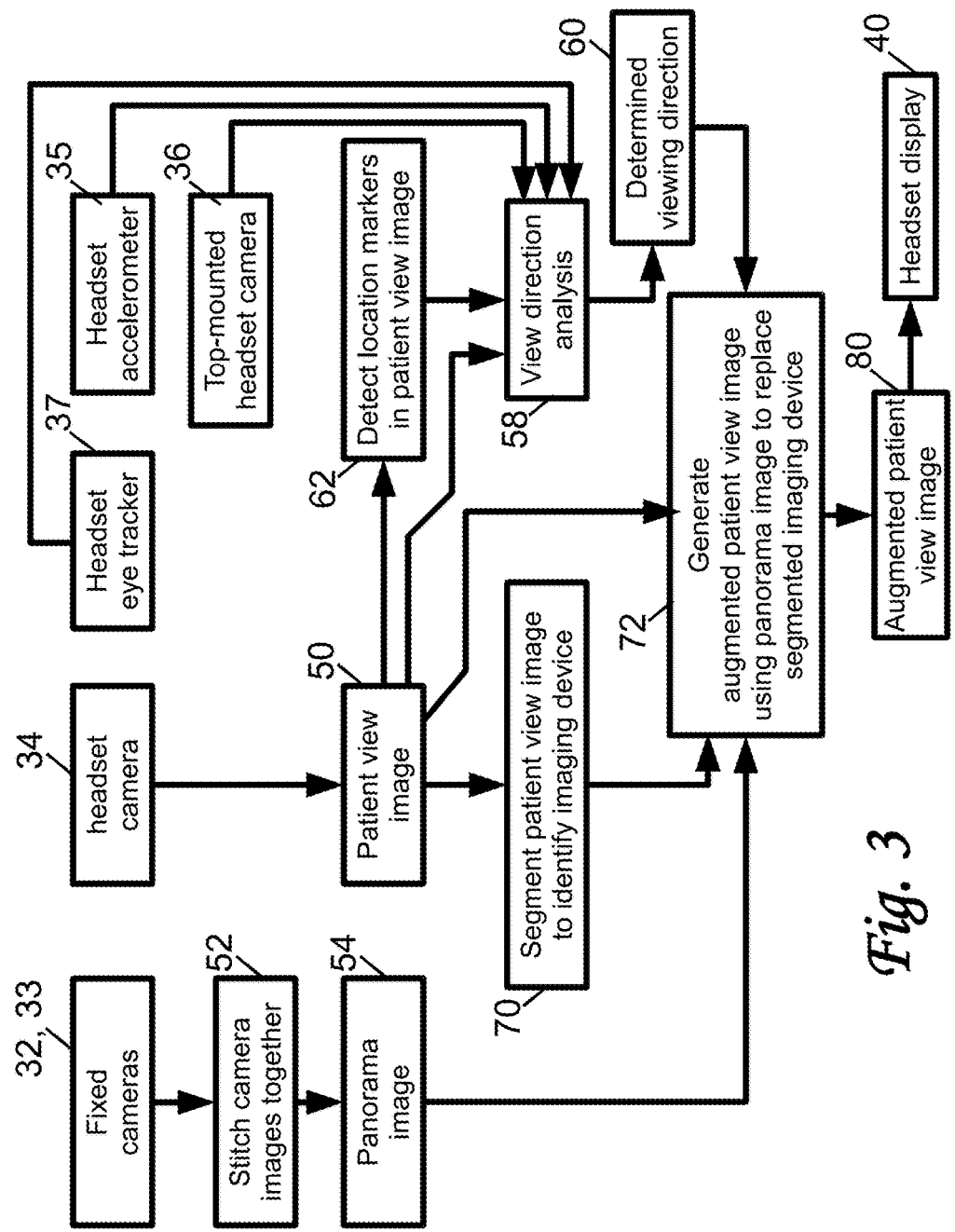
FIG. 3 diagrammatically illustrates an augmented reality display generation process suitably performed by the augmented reality device of FIG. 1.

With reference now to FIG. 3, an illustrative augmented reality (AR) image generation process suitably performed by the AR device of FIGS. 1 and 2 is described. It is to be understood the AR image generation process is performed in real-time to provide the patient or other imaging subject with a real-time (augmented) view of the imaging laboratory. Inputs include the images produced by the fixed cameras 32, 33, the patient view image 50 produced by the headset camera 34, and the other data indicative of viewing direction of the imaging subject output by the other directional sensors 35, 36, 37. In a stitching operation 52, the images captured by the fixed cameras 32, 33 are combined to produce a panorama image 54. The operation 52 can employ standard image stitching software to join images of adjacent fields-of-view at their (possibly overlapping) junctions, and making adjustments for different parallax of the constituent images. In some embodiments, corresponding portion(s) of the panorama image 54 are used as substitute images for removing, replacing, or making partially transparent the medical imaging device 10 in the augmented patient view image. Consequently, the panorama image 54 generally does not need to capture the medical image device 10. To provide suitable substitute image portions, the panorama image 54 should capture the range of possible views directed "outward" from the medical imaging device 10 looking along the patient's vantage point. Hence, for example, the illustrative MRI device-mounted cameras 32 are mounted on the medical imaging device 10 and oriented to look outward to generate suitable substitute image portions looking outward from the medical imaging device 10.

The data indicative of viewing direction of the imaging subject collected by the various directional sensors 34, 35, 36, 37 are processed in a view direction analysis 58 to determine the viewing direction 60 of the imaging subject. In one approach, an operation 62 processes the patient view image 50 to detect location markers in the patient view image 50 and thereby determine (or contribute to determining) the patient viewing direction 60. The location markers may include objects, doors, windows, or other features in the laboratory that can be readily identified in the patient view image 50 by matched filtering, comparison with reference images, or another object identification process. Additionally or alternatively, data from the accelerometer 35 can be used to determine head orientation (based on measuring the gravitational vector), and/or the top-mounted camera 36 can be used to provide a second vantage that can be compared with the vantage of the patient view image 50 to determine the viewing direction 60. The headset eye tracker 37 can be used to determine the gaze direction of the eyes relative to the head, so as to account for, e.g., whether the patient's eyes are pointed to the left, right, up, down, straight ahead, or so forth.

With brief reference to FIG. 4, in some embodiments the location markers detected in the operation 62 may include designated location markers. In the example of FIG. 4, the bore 16 is shown. When the patient's head is disposed inside the bore 16, the view is generally limited seeing the walls of the bore 16, which are conventionally featureless or nearly so. To assist in determining the viewing direction, in the embodiment of FIG. 4 a set of location markers 64 are marked on the bore walls to aid in viewing direction determination. The illustrative location markers 64 employ sets of dots to encode location, but any other visually perceptible encoding scheme may be similarly employed. While particularly useful inside the relatively featureless bore 16, intentionally applied location markers may be similarly placed on walls, the floor, and/or the ceiling of the laboratory.

While FIG. 4 addresses the situation of providing the AR when the patient is inside the bore 16 of the medical imaging device 10, in some embodiments the AR view is also provided when the patient is outside of the bore 16, for example as the patient is entering the imaging laboratory room 12. This provides the desired anxiety reduction at the key point just before the patient is loaded into the bore 16 and the imaging commences. To provide these "exterior" augmented views, additional camera such as the illustrative ceiling-mounted cameras 33, and optionally other cameras (not shown) providing panorama image components from other vantage points, e.g. wall-mounted cameras, door frame-mounted cameras, floor-mounted cameras, cameras mounted on other devices inside the laboratory room such as on the linac in the case of a radiation therapy setting, or so forth.

Rather than physical location markers, in another approach an optical system can be used to project an optical spatial encoding grid onto the bore walls, and/or onto the walls, ceiling, and/or floor of the laboratory. The optical spatial encoding grid may, for example, comprise straight horizontal and vertical lines of light projected onto the walls. Advantageously, if an object is placed into such a grid it will distort the straight lines in a predictable way, providing for three-dimensional (3D) spatial encoding. In some embodiments the projected grid may be presented using infrared light so as not to be visible the patient or medical personnel (but visible to the cameras which in such embodiments are designed to have infrared sensitivity). In the case of several projectors, e.g. one for each camera 32, 33, the projected patterns may be modulated or encoded with a time-dependent signal, such as a sine wave, so that the patterns are separable through filtering. Such encoding prevents potential errors due to overlapping patterns from multiple cameras.

The foregoing are merely illustrative examples of approaches for determining the viewing direction 60; more generally, any viewing direction determination approach may be used. In some embodiments, the headset cameras 34, 36 may comprise range cameras that provide 3D spatial information directly.

With returning reference to FIG. 3, the collected real-time information including the illustrative patient view image 50, panorama image 54, and determined viewing direction 60 are used to generate the augmented view. In one approach, the augmented view is generated starting with the patient view image 50. Any portion of the medical imaging device 10 that is captured in the patient view image 50 is identified by a segmentation operation 70, e.g. using matched filtering, comparison with reference images, or another object identification process. The identified (portion of the) medical imaging device captured in the patient view image 50 is removed or made partially transparent by substituting corresponding portion(s) of the panorama image 54, where "corresponding" is identified based on the determined viewing direction 60 and the known vantage points of the fixed cameras 32, 33 that captured the images stitched together to generate the panorama image 54, and or by leveraging spatial image registration of the patient view image 50 to the panorama image 54. The resulting augmented patient view image 80 is displayed on the display 40 of the headset 30. The processing shown in FIG. 3 is repeated continually to provide the augmented patient view image 80 which is updated in real-time. For stereo display embodiments, the augmented patient view image 80 includes offset left eye and right eye components that are presented to the patient using the respective left display 40L and right display 40R.

In embodiments in which medical imaging device is made partially transparent in the augmented patient view image 80 by substituting a corresponding portion of the panorama image 54, one contemplated approach uses alpha blending to combine the image of the medical imaging device 10 in the patient view image 50 with the corresponding portion of the panorama image 54, with the amount of transparency of the medical imaging device controlled by an alpha parameter.

The illustrative augmentation includes the medical imaging device 10 being removed, replaced, or made partially transparent in the augmented patient view image 80. However, other augmentation operations are contemplated. For example, the augmentation may similarly identify, segment, and remove (or replace, or make partially transparent) other medical devices that may be present in the imaging laboratory and that may make the patient anxious, such as a mechanical ventilator device, a pharmaceutical delivery device, local radio frequency coils used in the MRI examination, the linac along with the MRI in the case of an MRI/linac system, or so forth. The augmentation could entail other changes, such as adding stuffed animals or other children's toys to the augmented patient view image 80 in the case of a pediatric imaging examination.

In some embodiments, the disclosed augmented reality (AR) device may instead be used in a virtual reality (VR) mode for patients who prefer a fully artificial synthetic VR experience rather than an augmented view of the imaging laboratory. Thus, the patient who prefers VR may be shown a synthetic reality totally divorced from the reality of the imaging laboratory—in the VR mode the fixed cameras 32, 33 are not used, and the augmentation processing 70, 72 is replaced by VR processing that generates a VR image along the determined viewing direction 60. By contrast, for patients who are uncomfortable with the complete artificiality of the VR experience, or who need to have good situational awareness in order to cooperate with medical personnel during the imaging examination, the disclosed AR view is provided using the fixed cameras 32, 33 and the augmentation processing 70, 72 as described herein.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An augmented reality device for use in a medical imaging laboratory housing a medical imaging device, the augmented reality device comprising:
a headset having a display mounted on the headset to be viewed by an imaging subject when the headset is worn by the imaging subject;
cameras mounted at different positions in the medical imaging laboratory to acquire images of the medical imaging laboratory;
directional sensors mounted on the headset to collect data indicative of a viewing direction of the imaging subject;
at least one electronic processor; and
at least one non-transitory storage medium storing:
panorama image generating instructions readable and executable by the at least one electronic processor to stitch together the images of the medical imaging laboratory acquired by the cameras to generate a panorama image of the medical imaging laboratory;
viewing direction analysis instructions readable and executable by the at least one electronic processor to process the data indicative of the viewing direction of the imaging subject collected by the directional sensors and to output a determined viewing direction;
augmentation instructions readable and executable by the at least one electronic processor to process at least the panorama image of the medical imaging laboratory and the determined viewing direction to generate an augmented patient view image corresponding to the determined viewing direction and augmented at least by the medical imaging device being removed, replaced, or made partially transparent in the augmented patient view image within the medical imaging laboratory; and
headset operating instructions readable and executable by the at least one electronic processor to operate the headset to present the augmented patient view image from within the medical laboratory using the display mounted on the headset.

2. The augmented reality device of claim 1 wherein the cameras include cameras mounted on the medical imaging device and oriented to generate images looking outward from the medical imaging device.

3. The augmented reality device of claim 1 wherein the directional sensors mounted on the headset include: a headset camera mounted on the headset to provide a patient view image in the viewing direction of the imaging subject; wherein the augmentation instructions are readable and executable by the at least one electronic processor to process at least the panorama image and the determined viewing direction and the patient view image acquired by the headset camera to generate the augmented patient view image.

4. The augmented reality device of claim 3 wherein the augmentation instructions generate the augmented patient view image from the patient view image acquired by the headset camera by operations including at least removing or making partially transparent any portion of the medical imaging device in the patient view image by substituting corresponding portions of the panorama image.

5. The augmented reality device of claim 3 further comprising: location markers disposed on walls of a bore of the medical imaging device;
wherein the viewing direction analysis instructions are readable and executable by the at least one electronic processor to detect the location markers in the patient view image and to output the determined viewing direction at least in part based on the detected location markers in the patient view image.

6. The augmented reality device of claim 1 wherein the directional sensors include one or more of: a headset camera mounted on the headset; an accelerometer mounted on the headset; and an eye tracker mounted on the headset.

7. The augmented reality device of claim 1 wherein the headset comprises goggles or eyeglasses.

8. The augmented reality device of claim 1 wherein the headset further includes noise-reducing earphones configured to reduce or block external sound and to transmit a received audio signal.

9. The augmented reality device of claim 1 wherein the display mounted on the headset includes: a left eye display mounted on the headset to be viewed by a left eye of the imaging subject when the headset is worn by the imaging subject; and a right eye display mounted on the headset to be viewed by a right eye of the imaging subject when the headset is worn by the imaging subject.

10. A medical imaging system comprising: a medical imaging device including a housing with a bore into which an imaging subject is received for imaging; and an augmented reality device as set forth in claim 1.

11. The medical imaging system of claim 10 wherein the medical imaging device comprises one or more of a magnetic resonance imaging (MRI) device, a positron emission tomography (PET) imaging device, and a transmission computed tomography (CT) imaging device.

12. The medical imaging system of claim 10 wherein the cameras of the augmented reality device include cameras mounted on the medical imaging device and oriented to generate images looking outward from the medical imaging device.

13. An augmented reality method for use in a medical imaging laboratory housing a medical imaging device, the augmented reality method comprising:
acquiring a panorama image of the medical imaging laboratory using cameras mounted in the medical imaging laboratory;
determining a viewing direction of an imaging subject using an electronic processor operating on data acquired by directional sensors mounted on a headset worn by the imaging subject;
processing at least the panorama image and the determined viewing direction using the electronic processor to generate an augmented patient view image corresponding to the determined viewing direction and augmented at least by the medical imaging device being removed, replaced, or made partially transparent in the augmented patient view image within the medical imaging laboratory; and
presenting the augmented patient view image to the imaging subject using a display mounted on the headset worn by the imaging subject.

14. The augmented reality method of claim 13 further comprising:
acquiring a patient view image using a headset camera mounted on the headset worn by the imaging subject;
wherein the processing comprises processing at least the panorama image, the determined viewing direction, and the patient view image using the electronic processor to generate the augmented patient view image.

15. The augmented reality method of claim 14 wherein the processing comprises removing or making partially transparent any portion of the medical imaging device in the patient view image by substituting corresponding portions of the panorama image.

16. The augmented reality method of claim 14 wherein determining the viewing direction includes detecting location markers disposed on walls of a bore of the medical imaging device in the patient view image.

17. The augmented reality method of claim 13 further comprising: reducing sounds perceived by the imaging subject using noise-reducing earphones of the headset worn by the imaging subject.

18. The augmented reality method of claim 13 wherein the presenting comprises:
presenting the augmented patient view image to the imaging subject as a stereo display using a left eye display mounted on the headset to be viewed by a left eye of the imaging subject wearing the headset and a right eye display mounted on the headset to be viewed by a right eye of the imaging subject wearing the headset.

19. A non-transitory storage medium storing instructions readable and executable by at least one electronic processor to perform an augmented reality method for use in a medical imaging laboratory housing a medical imaging device, the stored instructions comprising:
panorama image generating instructions readable and executable by the at least one electronic processor to stitch together images acquired by cameras mounted in the medical imaging laboratory to generate a panorama image of the medical imaging laboratory;
viewing direction analysis instructions readable and executable by the at least one electronic processor to process the data indicative of the viewing direction of the imaging subject collected by directional sensors mounted on a headset worn by an imaging subject and to output a determined viewing direction;
augmentation instructions readable and executable by the at least one electronic processor to process at least the panorama image and the determined viewing direction to generate an augmented patient view image corresponding to the determined viewing direction and augmented at least by the medical imaging device being removed, replaced, or made partially transparent in the augmented patient view image within the medical imaging laboratory; and
headset operating instructions readable and executable by the at least one electronic processor to operate the headset worn by the imaging subject to present the augmented patient view image to the imaging subject using a display mounted on the headset.

20. The non-transitory storage medium of claim 19 wherein the augmentation instructions are readable and executable by the at least one electronic processor to process at least the panorama image and the determined viewing direction and a patient view image acquired by a headset camera mounted on the headset worn by the imaging subject to generate the augmented patient view image.

21. The non-transitory storage medium of claim 20 wherein the augmentation instructions generate the augmented patient view image from the patient view image acquired by the headset camera by operations including at least removing or making partially transparent any portion of the medical imaging device in the patient view image by substituting corresponding portions of the panorama image.

* * * * *